United States Patent [19]

Haake et al.

[11] 4,105,795
[45] Aug. 8, 1978

[54] ANTISPASMODIC SUBSTITUTED SULPHOXIMIDES

[75] Inventors: Manfred Haake, Marburg-Cappel; Reinhold Pothmann, Buergeln; Kurt H. Ahrens, Schwaig; Edgar Fritschi, Roethenbach, all of Fed. Rep. of Germany

[73] Assignee: Ludwig Heumann & Co. GmbH., Nuremburg, Fed. Rep. of Germany

[21] Appl. No.: 719,970

[22] Filed: Sep. 2, 1976

[30] Foreign Application Priority Data

Sep. 3, 1975 [DE] Fed. Rep. of Germany ....... 2539220

[51] Int. Cl.$^2$ .................... A61K 31/16; A61K 31/40; A61K 31/445; A61K 31/535; C07C 145/00; C07D 295/08

[52] U.S. Cl. ................................... 424/320; 260/544; 260/159; 260/85; 260/37; 260/293.57; 260/293.73; 260/293.85; 260/326.82; 260/327 TH; 260/327 P; 260/328; 260/329 AM; 260/329.3; 260/330.5; 260/501.15; 260/501.21; 260/551.5; 424/247; 424/248.5; 424/248.51; 424/267; 424/274; 424/275; 424/276; 424/316

[58] Field of Search .................... 260/551 S, 247.1 R, 260/293.73, 326.82, 501.15, 501.21; 424/248, 267, 274, 316, 320, 325, 330

[56] References Cited

U.S. PATENT DOCUMENTS 3,637,664  1/1972  Satzinger et al. ............ 260/551 S X

OTHER PUBLICATIONS

Satzinger et al., CA 82:111832k (1974).
Stoss et al., CA 78:124195x (1973).

*Primary Examiner*—Daniel E. Wyman
*Assistant Examiner*—Thomas A. Waltz
*Attorney, Agent, or Firm*—Bacon & Thomas

[57] ABSTRACT

This invention provides compounds of the general formula I

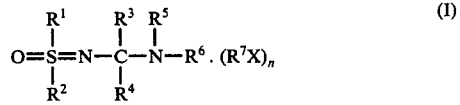

wherein $R^1$ and $R^2$ independently represent groups selected from the group consisting of straight chain alkyl groups; branched chain alkyl groups; aryl groups; optionally substituted aryl groups and the groups required to complete a ring system together with the sulphur atom;

$R^3$ and $R^4$ independently represent groups selected from the group consisting of hydrogen; straight chain alkyl groups; branched chain alkyl groups and optionally substituted aryl groups;

$R^5$ and $R^6$ independently represent groups selected from the group consisting of alkyl groups and the groups required to complete a heterocyclic ring together with the nitrogen atom; the group $R^7$ represents a group selected from the group consisting of hydrogen; straight chain alkyl groups and branched chain alkyl groups;

X represents an anion of a physiologically acceptable acid and n represents a number selected from the group consisting of 0 and 1.

The compounds show pharmacological activity, for example, as spasmolytics and broncholytics.

54 Claims, No Drawings

ANTISPASMODIC SUBSTITUTED SULPHOXIMIDES

SUMMARY OF THE INVENTION

This invention relates to new substituted sulphoximides, to a process for their preparation and to pharmaceutical compositions containing them.

In particular, the invention relates to substituted sulphoximides and their salts represented by the general formula I

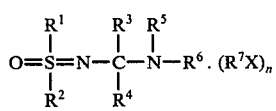

wherein the groups $R^1$ and $R^2$, independently represent groups selected from the group consisting of straight chain and branched chain alkyl groups; aryl groups and aralkyl groups which may be substituted and the groups required to complete a ring system together with the sulphur atom; the groups $R^3$ and $R^4$ independently represent groups selected from the group consisting of hydrogen atoms; straight chain and branched chain alkyl groups and aryl groups which may be substituted; the groups $R^5$ and $R^6$ independently represent groups selected from the group consisting of alkyl groups and the groups required to complete a heterocyclic ring together with the nitrogen atom; the group $R^7$ represents a group selected from the group consisting of hydrogen and straight chain and branched chain alkyl groups; X represents an anion of a physiologically acceptable acid and $n$ represent a number selected from the group consisting of 0 and 1.

This invention also provides a process for the preparation of these substituted sulphoximides and their salts in which an alkali metal compound of S,S-disubstituted sulphoximide is reacted in a solvent or dispersing agent with an iminium salt of the formula (II)

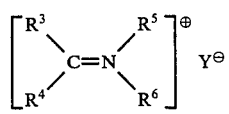

wherein $R^3$, $R^4$, $R^5$ and $R^6$ have the meaning specified above and Y denotes an anion and the reaction products are optionally converted into their ammonium salts in the usual manner.

The substituted sulphoximides of the general formula (I) mentioned above and their salts are new compounds.

In the general formula (I), the substituents $R^1$ and $R^2$ represent alkyl groups such as straight or branched chain alkyl groups having from 1 to 12, preferably 1 to 8, more preferably 1 to 6 and most preferably 1 to 3 carbon atoms, for example methyl, ethyl, n-propyl, isopropyl, n-butyl, isobutyl, pentyl or hexyl groups or cycloalkyl groups having from 5 to 8 carbon atoms such as cyclopentyl or cyclohexyl groups, aryl groups such as phenyl, naphthyl or diphenyl groups which may be substituted in the ortho, meta or para position by halogen atoms such as chlorine, bromine or fluorine atoms or by trifluoromethyl groups or by alkoxy groups having from 1 to 3 carbon atoms such as methoxy or ethoxy or by $C_1$-$C_3$ alkyl groups, or they may be disubstituted with the above mentioned substituents, as for example in the case of a chlorophenyl, methoxyphenyl or tolyl group. $R^1$ and $R^2$ may also represent aralkyl groups in which the alkyl portion may have from 1 to 3 carbon atoms, for example a benzylethyl or a phenylethyl group.

Alternatively, the groups $R^1$ and $R^2$ and the sulphur atom may together form a 5-membered or 6-membered ring system which may be condensed with aromatic radicals. Examples of such ring systems include thiacyclopentane; thiacyclohexane; 1,4-thioxane; isothiochroman; benzothiophene; dibenzothiophene; thioxanthene; phenoxthine; thianthrene or a phenothiazine group which may be N-substituted.

The groups $R^3$ and $R^4$ represent alkyl groups such as straight or branched chain alkyl groups having from 1 to 12, preferably 1 to 8, more preferably 1 to 6 and most preferably 1 to 3 carbon atoms, for example methyl, ethyl, n-propyl, isopropyl, n-butyl, isobutyl, pentyl or hexyl groups or cycloalkyl groups having from 5 to 8 carbon atoms such as cyclopentyl or cyclohexyl groups, aryl groups such as phenyl, naphthyl or diphenyl groups which may be substituted in the ortho, meta or para position by halogen atoms such as chlorine, bromine or fluorine atoms or by trifluoromethyl groups or by alkoxy groups having from 1 to 3 carbon atoms such as methoxy or ethoxy or by $C_1$-$C_3$ alkyl groups, or they may be disubstituted with the above mentioned substituents, for example they may represent a chlorophenyl, methoxyphenyl or tolyl group.

The groups $R^5$ and $R^6$ represent alkyl groups such as straight or branched chain alkyl groups having from 1 to 12, preferably 1 to 8, more preferably 1 to 6 and most preferably 1 to 3 Carbon atoms, for example methyl, ethyl, n-propyl, isopropyl, n-butyl, isobutyl, pentyl or hexyl groups or cycloalkyl groups having from 5 to 8 carbon atoms such as cyclopentyl or cyclohexyl groups.

The groups $R^5$ and $R^6$ may also form a heterocyclic ring together with the nitrogen atom. This ring may also contain another hetero atom such as a nitrogen, oxygen or sulphur atom, for example it may be a piperidine, morpholine or pyrrolidine ring.

The group $R^7$ represents a hydrogen atom or an alkyl group, e.g. a lower alkyl group having from 1 to 6, preferably 1 to 3 carbon atoms, e.g. a methyl, ethyl, n-propyl, isopropyl, n-butyl, isobutyl, pentyl or hexyl group.

X represents an inorganic or organic anion of a physiologically acceptable acid such as, for example, hydrochloric acid, hydrobromic acid, phosphoric acid, acetic acid, maleic acid, tartaric acid, lactic acid, perchloric acid or methylsulphuric acid.

The reaction of the alkali meal compound of S,S-disubstituted sulphoximide with the iminium salt proceeds in accordance with the following reaction scheme:

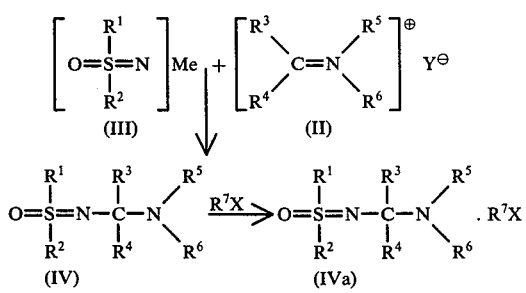

In the above formulae, Me represents an alkali metal and Y may be, for example, a halogen, perchlorate or fluoroborate anion.

The reaction of the iminium salts (II) which are sensitive to hydrolysis, is carried out with the exclusion of moisture in a solvent or dispersing agent such as benzene, tetrahydrofuran or acetonitrile at a temperature of between about −20° C and about 60° C. Highly reactive iminium salts are preferably reacted at lower temperatures and the less reactive ones at temperatures up to 60° C. The reactants are used in substantially equivalent quantities although one of the starting compounds may be used in excess. Conversion of the bases (IV) into the salts (IVa) is preferably carried out under conditions of quaternisation by means of the usual alkylation methods in anhydrous, inert solvents such as ether or acetonitrile with the addition of $R^7X$.

The compounds according to the invention of formulae (I), (IV) and (IVa) show pharmacological activity, e.g. as spasmolytics, which make them appear suitable for use as pharmaceutical compositions.

The substances according to the invention were tested for their spasmolytic and their broncholytic action both in vivo and in vitro. They proved to be efficient spasmolytics with a neurotropic and musculotropic action when compared with atropine. They provided long lasting relief for bronchospasms produced by histamine and acetyl choline. The beneficial effect after introgastric or introduodenal administration indicates good entrail absorption. When tested for acute toxicity, the substances according to the invention proved to be relatively nontoxic. An $LD_{50}$ administered introgastrally to mice is greater than 1600 mg/kg. In contrast to atropine, the compounds acording to the invention are equally antagonistic to spasms produced by histamine as to spasms produced by barium chloride.

The invention also relates to pharmaceutical compositions containing an effective quantity of the compound according to the invention represented by the general formula (I) in addition to the usual diluents and excipients.

The compounds according to the invention may be made up into the usual forms of pharmaceutical preparations, i.e. tablets, capsules, coated tablets, drops, suppositories or injections.

They may be administered orally, rectally or by injection.

The invention will now be explained with the aid of the following non-limiting Examples.

SPECIFIC EMBODIMENTS

EXAMPLE 1

N-(Diethylamino-methyl)-S-methyl-S-phenyl-sulphoximide

A suspension of 0.05 mol of the sodium salt of S-methyl-S-phenyl-Sulphoximide and 0.05 mol of diethylamino-methylene iminium chloride in 150 ml of absolute benzene was stirred for 2 hours with the exclusion of moisture at room temperature, filtered and freed from benzene in a vacuum. 11.8 g (97%) of practically pure product were obtained in the form of a yellowish oil which was hygroscopic and decomposed on distillation under vacuum.

Formula: $C_{12}H_{20}H_2OS$; Molecular weight: 240.40 1H-NMR-spectrum in $CCl_4$ ($\delta$ in ppm):

$CH_3$ (3.0); $C_6H_5$ (7.5; 7.9); $CH_2$ (3.8); $N(C_2H_5)_2$ (2.6; 1.0).

EXAMPLE 2

N-(Piperidino-methyl)-S-methyl-S-phenyl-sulphoximide and its methyl-piperidinium-bromide A suspension of 0.03 mol of the sodium salt of S-methyl-S-phenyl-sulphoximide and 0.03 mol of N-piperidinomethylene-iminium chloride in 80 ml of Benzene was stirred with the exclusion of moisture at room temperature for 2 hours, filtered and freed from benzene under vacuum. 6.6 g (85%) of practically pure product were obtained in the form of a yellowish viscous oil which crystallised when left to stand for some time in a refrigerator and decomposed on distillation under vacuum.

Formula: $C_{13}H_{20}N_2OS$; Molecular weight: 252.4 1H-NMR-spectrum in $CCl_4$ ($\delta$ in ppm):

$CH_3$ (3.0); $C_6H_5$ (7.4; 7.8); $CH_2$ (3.7); N $(CH_2)_5$ (2.4; 1.4).

Conversion into the methyl-piperidinium bromide was carried out by a similar procedure to that of Example 3. The yield was almost quantitative Formula: $C_{14}H_{23}N_2OSBr$; Molecular weight: 347.4 1H-NMR-spectrum in $CDCl_3$ ($\delta$ in ppm):

$SCH_3$ (3.2); $C_6H_5$ (7.6; 7.9); $CH_2$ (4.6); $NCH_3$ (3.3); $N(CH_2)_5$ (3.2; 1.8).

EXAMPLE 3

N-(Dimethylamino-methyl)-S,S-diphenyl-sulphoximide and its trimethyl-ammonium bromide A suspension of 0.05 mol of the sodium salt of S,S-diphenylsulphoximide and 0.05 mol of dimethylaminomethylene-iminium chloride in 150 ml of absolute benzene was stirred at room temperature for 2 hours with the exclusion of moisture, filtered and freed from benzene under vacuum. 13.5 g (98%) of product which was practically analytically pure were obtained in the form of a yellowish oil which became crystalline when left to stand in the refrigerator and decomposed on distillation under vacuum.

Formula: $C_{15}H_{18}N_2OS$; Molecular weight: 274.4 1H-NMR-spectrum in $CCl_4$ ($\delta$ in ppm):

$C_6H_5$ (8.0; 7.5); $CH_2$ (3.9); $N(CH_3)_2$ (2.3).

To convert the oily base into the trimethyl-ammonium bromide, it was dissolved in absolute ether and cooled to −20° C. A fivefold excess of methyl bromide was added and the mixture was tightly sealed and left to stand at room temperature. The practically pure quaternary salt (decomposition starting at 150° C) was obtained in almost quantitative yields.

Formula: $C_{16}H_{21}N_2OSBr$; Molecular weight: 369.4 1H-NMR-spectrum in $CDCl_3$ ($\delta$ in ppm): trimethyl ammonium $C_6H_5$ (7.5; 7.9); $CH_2$ (4.7); $N(CH_3)_3$ (3.4).

EXAMPLE 4

N-($\alpha$-dimethylamino-benzyl)-S,S-diphenyl-sulphoximide and its trimethylammonium bromide A suspension of 0.05 mol of the sodium salt of S,S-diphenyl-sulphoximide and 0.05 mol of dimethylaminobenzylidene-iminium chloride in 150 ml of absolute benzene was stirred at room temperature for 5 hours with the exclusion of moisture, filtered and freed from benzene. The product was obtained in about 90% yield as a yellow oil which crystallised when left to stand in the refrigerator.

Formula: $C_{12}H_{22}N_2OS$; Molecular weight: 350.5 1H-NMR-spectrum in $CCl_4$ (δ in ppm):
$SC_6H_5$ (7.4; 8.0); $CC_6H_5$ (7.3); CH (4.8); $N(CH_3)_2$ (2.2).

Conversion into the trimethyl-ammonium bromide was carried out by a similar procedure to that of Example 3 and the quaternary salt was obtained in the form of colourless crystals.

Formula: $C_{22}H_{25}N_2OSBr$; Molecular weight: 445.5 1H-NMR-spectrum in $CDCl_3$ (δ in ppm).
$SC_6H_5$ (7.5; 8.0); $CC_6H_5$ (7.3); CH (5.4); $N(CH_3)_3$ (2.9).

EXAMPLE 5

N-(piperidino-methyl)-S,S-dimethyl-sulphoximide

A suspension of 0.03 mol of the sodium salt of S,S-dimethylsulphoximide and 0.03 mol of N-piperidinomethylene-iminium chloride in 100 ml of absolute benzene was stirred at room temperature for 2 hours with the exclusion of moisture, filtered and freed from benzene under vacuum. 4.9 g (86%) of practically pure product were obtained in the form of a yellowish oil which tended to change into the symmetrical isomers, bis-piperidino-methane- and methylene-bis-sulphoximide when heated.

Formula: $C_8H_{18}N_2OS$; Molecular weight: 190.3 1H-NMR-spectrum in $CDCl_3$ (δ in ppm):
$SCH_3$ (3.0); $CH_2$ (3.8); $N(CH_2)_5$ (2.4; 1.5).

EXAMPLE 6

N-(Piperidino-methyl)-S-n-butyl-S-methyl-sulphoximide

The preparation was similar to that of Example 5. The product was a hydroscopic almost colourless oil. The yield was 6.2 g (88%).

Formula: $C_{11}H_{24}N_2OS$; Molecular weight: 232.4 1H-NMR-spectrum in $CDCl_3$ (δ in ppm):
$CH_3$ (2.9); n-butyl (3.1; 1.6; 1.0); $CH_2$ (3.8); $N(CH_2)_5$ (2.4; 1.5).

EXAMPLE 7

N-(Piperidino-methyl)-tetrahydrothiophene-S,S-oximide

The preparation was similar to that of Example 5. The product was a hygroscopic, almost colourless oil. The yield was 6.3 g (97%).

Formula: $C_{10}H_{20}N_2OS$; Molecular weight: 216.3 1H-NMR-spectrum in $CDCl_3$ (δ in ppm):
$(CH_2)_4S$ (3.1; 2.2); $CH_2$ (3.8); $N(CH_2)_5$ (2.4; 1.5).

EXAMPLE 8

N-(piperidino-methyl)-phenoxthine-S,S-oximide and its methyl-piperidinium bromide The preparation was similar to that of Example 5. The product was a yellowish, hygroscopic oil. The yield was 6.2 g (94%), Formula: $C_{18}H_{20}N_2O_2S$; Molecular weight: 328.4 1H-NMR-spectrum in $CDCl_3$ (δ in ppm):
Phenoxthiene (8.0; 7.4); $CH_2$ (3.8); $N(CH_2)_5$ (2.3; 1.3).

For conversion into the methyl-piperidinium bromide, the base was dissolved in absolute ether and cooled to −40° C. A fivefold excess of methyl bromide was then added and the mixture was stirred overnight while it was slowly warmed up to room temperature. The almost analytically pure salt (Mp 128° – 129° C) was obtained in practically quantitative yield.

Formula: $C_{19}H_{23}BrN_2O_2S$; Molecular weight: 423.4 1H-NMR-spectrum in $d_6$-DMSO (δ in ppm):
Phenoxthiene (8.2; 7.6); $CH_2$ (4.6); $N(CH_2)_5$ (3.3; 1.7); $NCH_3$ (3.0).

EXAMPLE 9

N-(Dimethylamino-methyl)-phenoxthiene-S,S-oximide and its trimethyl-ammonium-bromide The preparation was similar to that of Example 5 and the product was a yellowish hygroscopic oil;
The yield was 8.0 g (93%)

Formula: $C_{15}H_{16}N_2O_2S$; Molecular weight: 288.4 1H-NMR-spectrum in $CDCl_3$ (δ in ppm);
Phenoxthiene (7.9; 7.3); $CH_2$ (3.8); $N(CH_3)_2$ (2.1).

The production of the trimethyl ammonium-bromide was similar to that of Example 8. The yield was quantitative Formula: $C_{16}H_{19}BrN_2O_2S$; Molecular weight: 382.3 1H-NMR-spectrum in $d_6$-DMSO (δ in ppm);
Phenoxthiene (8.2; 7.6); $CH_2$ (4.6); $N(CH_3)_3$ (3.0).

The following compounds, among others, can also by synthesised by methods corresponding to those of Examples 1 to 9:

EXAMPLE 10

N-(α-dimethylamino-benzyl)-S,S-dimethyl-sulphoximide and its trimethyl-ammonium-bromide.

EXAMPLE 11

N-(α-morpholino-tolyl)-S-n-butyl-S-methyl-sulphoximide and its methyl-morpholinium-methosulphate.

EXAMPLE 12

N-Dimethylamino-methyl-S-methyl-S-(β-phenylethyl)-sulphoximide and its trimethyl-ammonium bromide.

EXAMPLE 13

N-(α-dimethylamino-α,α-diphenyl-methyl)-S,S-dimethyl-sulphoximide.

EXAMPLE 14

N-(α-pyrrolidino-α-isopropyl-methyl)-S,S-diphenyl-sulphoximide and its perchlorate.

EXAMPLE 15

N-(α-dimethylamino-α,α-diphenyl-methyl)-S,S-diphenylsulphoximide.

EXAMPLE 16

N-(α-morpholino-p-chlorobenzyl)-S,S-diphenyl-sulphoximide.

EXAMPLE 17

N-diethylamino-methyl-S-phenyl-S-cyclohexyl-sulphoximide and its methyl-diethyl-ammonium-iodide.

EXAMPLE 18

N-(α-dimethylamino-α,α-diphenyl-methyl)-S-phenyl-S-cyclohexylsulphoximide.

EXAMPLE 19

N-diethylamino-methyl-S-phenyl-S-(β-phenylethyl)-sulphoximide and its methyl-diethyl-ammonium bromide.

EXAMPLE 20

N-dimethylamino-methyl-S,S-(p-methoxyphenyl)-sulphoximide and its trimethylammonium-bromide.

EXAMPLE 21

N-piperidino-methyl-S,S-(p-tolyl)-sulphoximide and its methyl-piperidinium-bromide.

EXAMPLE 22

N-(α-pyrrolidino-α-isopropyl-methyl)-thiacyclohexane-S,S-oximide and its methyl-pyrrolidinium-methosulphate.

EXAMPLE 23

N-dimethylamino-methyl-thioxanthene-S,S-oximide and its hydrochloride.

EXAMPLE 24

N-piperidino-methyl-dibenzothiophene-S,S-oximide and its methyl-piperidinium-chloride.

We claim:

1. Compounds of the general formula I

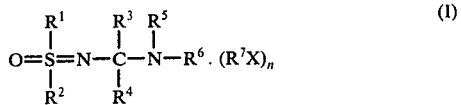

wherein
- $R^1$ represents a group selected from the group consisting of straight chain alkyl groups; branched chain alkyl groups; aryl groups; and aryl groups mono- or di- substituted by halogen, trifluoromethyl, alkoxy of 1 to 3 carbon atoms, or alkyl of 1 to 3 carbon atoms;
- $R^2$ represents an alkyl group;
- $R^3$ and $R^4$ independently represent groups selected from the group consisting of hydrogen; straight chain alkyl groups; branched chain alkyl groups; aryl groups and aryl groups mono- or di- substituted by halogen, trifluoromethyl, alkoxy of 1 to 3 carbon atoms, or alkyl of 1 to 3 carbon atoms;
- $R^5$ and $R^6$ are alkyl or together with the nitrogen atom form a piperidine, morpholine, or pyrrolidine ring, the group
- $R^7$ represents a group selected from the group consisting of hydrogen; straight chain alkyl groups and branched chain alkyl groups;
- X represents an anion of a physiologically acceptable acid and
- n represents a number selected from the group consisting of 0 and 1.

2. Compound according to claim 1 wherein $R^1$ and $R^2$ represent alkyl groups having from 1 to 12 carbon atoms.

3. Compound according to claim 1 wherein $R^1$ and $R^2$ represent alkyl groups having from 1 to 8 carbon atoms.

4. Compound according to claim 1 wherein $R^1$ and $R^2$ represent alkyl groups having from 1 to 6 carbon atoms.

5. Compound according to claim 1 wherein $R^1$ and $R^2$ represent alkyl groups having from 1 to 3 carbon atoms.

6. Compound according to claim 1 wherein $R^1$ represents a cycloalkyl group having 5 to 8 carbon atoms.

7. Compound according to claim 1 wherein $R^1$ represents an aryl group selected from the group consisting of phenyl; naphthyl and diphenyl groups.

8. Compound according to claim 1 wherein $R^1$ represents an aralkyl group wherein the alkyl portion has from 1 to 3 carbon atoms.

9. Compound according to claim 1 wherein $R^3$ and $R^4$ represent alkyl groups having from 1 to 12 carbon atoms.

10. Compound according to claim 1 wherein $R^3$ and $R^4$ represent alkyl groups having from 1 to 8 carbon atoms.

11. Compound according to claim 1 wherein $R^3$ and $R^4$ represent alkyl groups having from 1 to 6 carbon atoms.

12. Compound according to claim 1 wherein $R^3$ and $R^4$ represent alkyl groups having from 1 to 3 carbon atoms.

13. Compound according to claim 1 wherein $R^3$ and $R^4$ represent cycloalkyl groups having 5 to 8 carbon atoms.

14. Compound according to claim 1 wherein $R^3$ and $R^4$ represent aryl groups selected from the group consisting of phenyl; naphthyl and diphenyl groups.

15. Compound according to claim 1 wherein $R^5$ and $R^6$ represent alkyl groups having from 1 to 12 carbon atoms.

16. Compound according to claim 1 wherein $R^5$ and $R^6$ represent alkyl groups having from 1 to 8 carbon atoms.

17. Compound according to claim 1 wherein $R^5$ and $R^6$ represent alkyl groups having from 1 to 6 carbon atoms.

18. Compound according to claim 1 wherein $R^5$ and $R^6$ represent alkyl groups having from 1 to 3 carbon atoms.

19. Compound according to claim 1 wherein $R^5$ and $R^6$ represent cycloalkyl groups having 5 to 8 carbon atoms.

20. Compound according to claim 1 wherein $R^7$ represents an alkyl group having 1 to 6 carbon atoms.

21. Compound according to claim 1 wherein $R^7$ represents an alkyl group having 1 to 3 carbon atoms.

22. Compound according to claim 1 wherein X represents the anion of an acid selected from the group consisting of hydrochloric; hydrobromic; phosphonic; acetic; maleic; tartaric; lactic; perchloric and methylsulphonic acids.

23. N-(Diethylamino-methyl)-S-methyl-S-phenyl-sulphoximide.

24. N-(Piperidino-methyl)-S-methyl-S-phenyl-sulphoximide.

25. N-(Piperidino-methyl)-S-methyl-S-phenyl-sulphoximidemethyl-piperidinium-bromide.

26. N-(α-dimethylamino-benzyl)-S,S-diphenyl-sulphoximide.

27. N-(α-dimethylamino-benzyl)-S,S-diphenyl sulphoximide trimethyl ammonium bromide.

28. N-(Piperidino-methyl)-S,S-dimethyl-sulphoximide.

29. N-(Piperidino-methyl)-S-n-butyl-S-methyl-sulphoximide.

30. N-(α-dimethylamino-benzyl)-S,S-dimethyl-sulphoximide.

31. N-(α-dimethylamino-benzyl)-S,S-dimethyl-sulphoximide trimethyl-ammonium-bromide.

32. N-(α-morpholino-tolyl)-S-n-butyl-S-methyl-sulphoximide.

33. N-(α-morpholino-tolyl)-S-n-butyl-S-methyl-sulphoximide methyl-morpholinium-methosulphate.

34. N-Dimethylamino-methyl-S-methyl-S-(β-phenylethyl)-sulphoximide.

35. N-Dimethylamino-methyl-S-methyl-S-(β-phenylethyl)-sulphoximide trimethyl-ammonium-bromide.

36. N-(α-dimethylamino-α,α-diphenyl-methyl)-S,S-dimethylsulphoximide.

37. N-(α-dimethylamino-α,α-diphenyl-methyl)-S,S-diphenylsulphoximide.

38. N-(α-morpholino-p-chlorobenzyl)-S,S-diphenyl-sulphoximide.

39. N-diethylamino-methyl-S-phenyl-S-cyclohexyl-sulphoximide.

40. N-diethylamino-methyl-S-phenyl-S-cyclohexyl-sulphoximide methyl-diethyl-ammonium-iodide, 41. N-(α-dimethylamino-α,α-diphenyl-methyl)-S-phenyl-S-cyclohexyl-sulphoximide.

42. N-diethylamino-methyl-S-phenyl-S-(β-phenylethyl)-sulphoximide.

43. N-diethylamino-methyl-S-phenyl-S-(β-phenylethyl)-sulphoximide methyl-diethyl-ammonium-bromide.

44. N-dimethylamino-methyl-S,S-(p-methoxyphenyl)-sulphoximide.

45. N-dimethylamino-methyl-S,S-(p-methoxyphenyl)-sulphoximide trimethylammonium-bromide.

46. N-piperidino-methyl-S,S-(p-tolyl)-sulphoximide.

47. N-piperidino-methyl-S,S-(p-tolyl)-sulphoximide methyl-piperidinium-bromide.

48. Pharmaceutical compositions comprising an antispasmodically effective amount of a compound according to claim 1 in admixture with a pharmaceutically acceptable diluent.

49. Pharmaceutical compositions according to claim 48 which are in a form selected from the group consisting of tablets, capsules, crated tablets, drops, suppositories and injections.

50. Method of treating a patient suffering from spasms by administering an antispasmodically effective amount of a compound according to claim 1.

51. Method according to claim 50 wherein said compound is administered orally.

52. Method according to claim 50 wherein said compound is administered rectally.

53. Method according to claim 50 wherein said compound is administered by injection.

54. The pharmaceutical composition as defined in claim 48 wherein said compound is N-(diethylamino methyl)-S-methyl-S-phenyl-sulphoximide.

* * * * *